United States Patent [19]
Mueller

[11] Patent Number: 6,095,815
[45] Date of Patent: Aug. 1, 2000

[54] PAIR OF FORCEPS FOR APPLYING OF AN ARTICULATING FILM TO TEETH IN DENTISTRY

[75] Inventor: Peter Mueller, Ebersbach/Fils, Germany

[73] Assignee: Dr. Jean Bausch KG, Cologne, Germany

[21] Appl. No.: 09/309,892

[22] Filed: May 11, 1999

[30] Foreign Application Priority Data

Dec. 8, 1998 [DE] Germany ............................ 298 21 845

[51] Int. Cl.[7] ........................................................ A61C 3/14
[52] U.S. Cl. ............................................. 433/159; 606/205
[58] Field of Search ................................. 433/159, 70, 4; 606/205, 206, 207, 210

[56] References Cited

U.S. PATENT DOCUMENTS 1,518,021 12/1924 Truxillo ................................... 433/159
4,340,369 7/1982 Steiner et al. ........................... 433/162

Primary Examiner—John J. Wilson
Attorney, Agent, or Firm—Diller, Ramik & Wright, PC

[57] ABSTRACT

A pair of forceps for marking points of contact by means of an articulating film for use in dentistry is fork-shaped with two spaced arm pairs, the arms being angled by an angle of at least 60° in the end portions forming the clamps. The clamps are provided with gripping clamping surfaces.

17 Claims, 1 Drawing Sheet

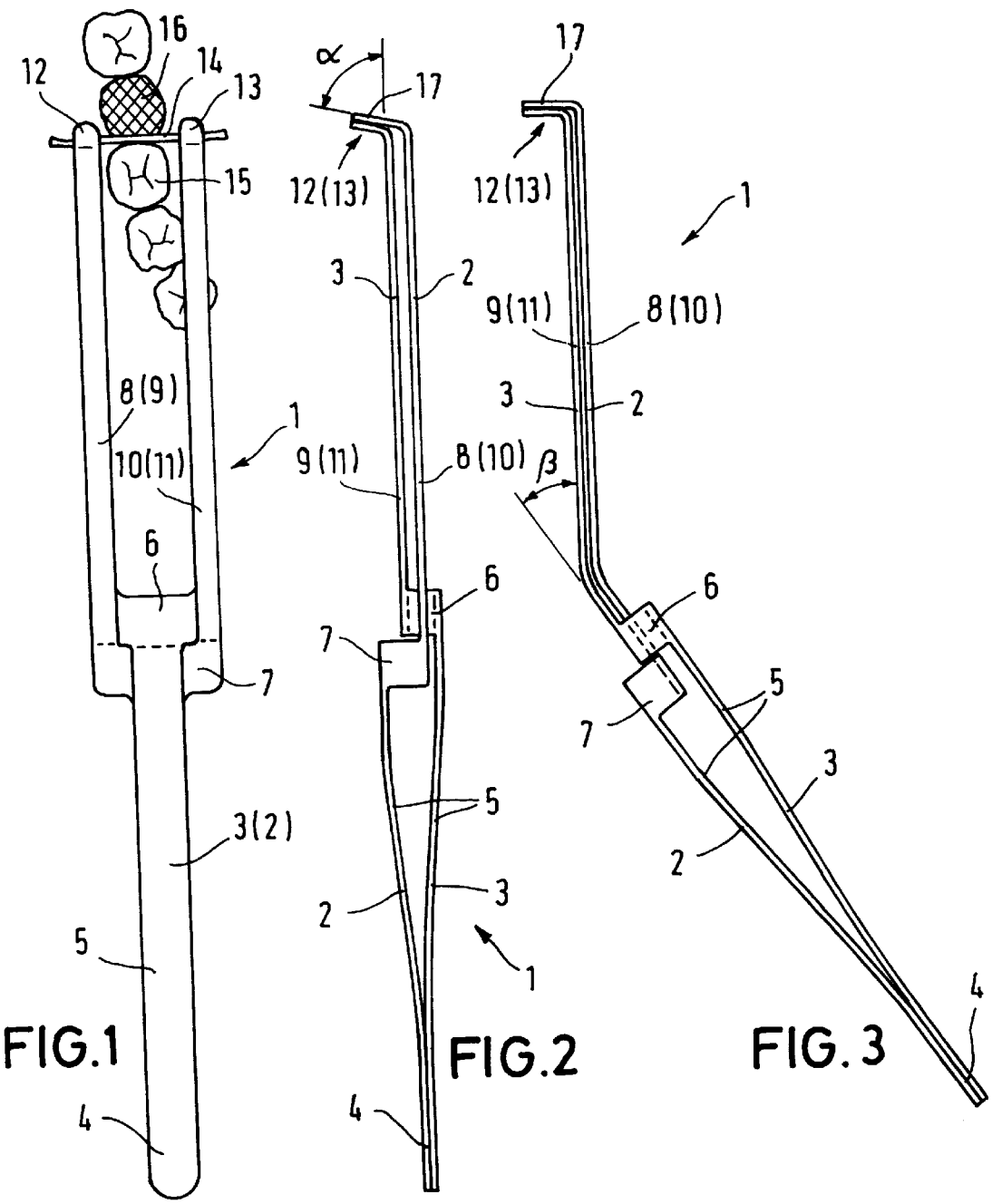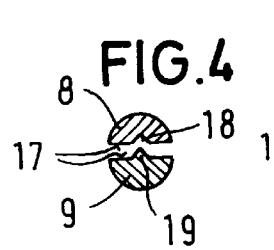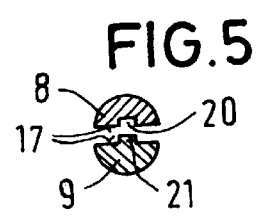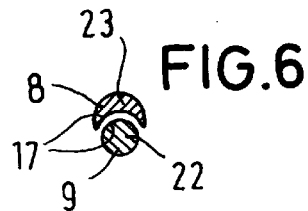

PAIR OF FORCEPS FOR APPLYING OF AN ARTICULATING FILM TO TEETH IN DENTISTRY

BACKGROUND OF THE INVENTION

The present invention is directed to a pair of forceps for marking points of contact by means of an articulating film for use in dentistry.

The present pair of forceps is used to control the approximate contacts between a tooth and a dental prosthesis to be integrated adjacent this tooth, where the dental prosthesis may be a crown, a bridge, an inlay, a partial crown, an onlay or a veneer. Here, the articulating film between the tooth and the dental prosthesis using the pair of forceps, the color emitted by the film onto the dental prosthesis indicating the area and the surface pressure of the approximate contact between the dental prosthesis and the tooth.

An instrument is known that has two members adapted to be displaced towards each other, the members having two arms with clamping elements for the articulating film at the ends of both arms. Both members are spring biased such that the clamping elements are pressed against each other to hold the articulating film. Between the clamping elements of both arms, the articulating film is held stretched. This instrument has at least three separate parts and has to be considered problematic with regard to cleaning, disinfection and sterilization, since the interengaging parts obstruct these necessary measures.

SUMMARY OF THE INVENTION

Thus, it is the object of the present invention to provide a pair of forceps for the above purpose, which also holds the articulating film in a taught manner.

The pair of forceps of the present invention is a one-piece device and, therefore, it is not only more simple and more economical to produce than the known instrument, but it is also very easy and safe to clean, to disinfect and to sterilize.

The pair of forceps may be designed as a self-opening, gripping pair of forceps that is closed by pressure. Preferably, however, the pair of forceps is constructed as a self-closing device to be opened by applying pressure. This design is advantageous in that no consideration has to be given to keeping the pair of forceps closed during use, so that attention can be given fully to the fitting of the dental prosthesis.

Since the gaps between the teeth into which the articulating film is to be inserted are almost perpendicular to the plane of occlusion, the clamping surfaces of the pair of forceps also have to be almost perpendicular to the longitudinal axis of the pair of forceps or at least to its arms. Since the clamping surfaces must open up, they have to be inclined under an angle of less than 90° with respect to a plane the arms of the pair of forceps move near to or away from when being closed or opened, respectively.

In a first embodiment concerning a straight pair of forceps, the above plane extends in the longitudinal direction of the pair of forceps and in parallel to the arms thereof. Here, the end portions of the arms forming the clamping surfaces are inclined under an angle of less than 90° with respect to the arms. Such a pair of forceps is handled just like conventional straight pairs of forceps and requires no change of handling.

In a second embodiment, the handle portion and the arm portion of the two parts of the pair of forceps are inclined towards each other—the above plane extends through the center of the handle portion of the forceps. In this case, the clamping surfaces may be perpendicular to the arms, since they are nevertheless inclined towards the above plane. Such a pair of forceps is advantageous in that the arms are positioned beside the row of teeth, thereby obstructing neither the view to the site nor the access thereto.

To ensure a secure holding of the articulating film, the clamping surfaces of the arms may be designed in a gripping manner, as defined in the dependent claims.

BRIEF DESCRIPTION OF THE DRAWINGS

The following is a detailed description of the invention with reference to the accompanying drawing illustrating embodiments of the present pair of forceps.

FIG. 1 is a top plan view of the pair of forceps;

FIGS. 2 and 3 are side elevational views of two different embodiments of the pair of forceps; and FIGS. 4 to 6 are sectional views of different embodiments of the clamps.

DETAILED DESCRIPTION OF THE PREFERRED EMBODIMENTS

The present pair of forceps 1 comprises to resilient parts 2 and 3, firmly attached at the rear end 4 of the forceps. Adjoining the rear end, the parts 2 and 3 have handles 5 and pass into arms at their front parts. The parts 2 and 3, respectively, split at the transition from the handles 5 to the arms via transverse webs 6 and 7 into paired, preferably parallel arms 8 and 9 and 10 and 11, respectively, the ends of which terminate in clamps 12 and 13. In the Figures, the reference numerals of the hidden arms are set in parentheses.

The present forceps 1 is a self-closing forceps, i.e., a pair of forceps closing due to the resilience of the two parts 2 and 3 and being opened by applying pressure on the handles 5. With the forceps 1 or its clamps 12 and 13 opened, a strip of articulating film 14 may be inserted between these clamps, which strip is then held self-actingly after the pair of forceps is closed by releasing the pressure on the handles 5.

Subsequently, using the forceps 1, the articulating film 14 thus held may inserted into the gap between the tooth 15 and, for example, a crown 16 to be positioned so as to cause a color stain representing the approximate contact. It is obvious that the articulating film 14 should be held in the gap as vertically as possible. Therefore, the clamping surfaces of the clamps 12 and 13 should at least form a right angle with the longitudinal axis of the forceps 1 or the arm pairs 8/9 and 10/11, respectively.

For the clamps 12 and 13 to open when the handles 5 are pressed and the arm pairs 8/9 and 10/11, respectively, move apart, the clamping surfaces 17 still have to be inclined with respect to an imaginary plane extending through the surface in which both parts of the forceps 1 are connected at the rear end 4. Since the articulating film 14 is very thin, a slight opening of the clamps 12 and 13 will already be enough to insert the articulating film.

In the embodiment of FIG. 2, the pair of forceps 1 or its parts 2 and 3 are straight. The end portions of the arms 8 to 11, forming the clamps 12 and 13, are thus angled by an angle alpha between 75° and 85°.

In the embodiment of FIG. 3, the handles 5 and the arms 8 to 11 of the forceps 1 are inclined towards each other under an angle beta between 20° and 30°. In this case, the ends of the arms 8 to 11 forming the clamps 12 and 13 may be angled by an angle alpha' of 90°.

In order to ensure a secure holding of the articulating film 14, the clamping surfaces 17 of the clamps 12, 13 may be fluted in a manner not shown in detail. Preferably, they are provided with engaging profiles. As illustrated in FIG. 4, these may be raised and recessed engaging prisms 18, 19, or engaging angular bars 20, 21 as in FIG. 5 or, as illustrated in FIG. 6, a cylindrical clamping jaw 22 mating with a matching half shell 23.

These engaging prisms 18, 19, the bars 20, 21 and the clamping jaws 22 with the half shells 23 provide for a particularly good grip when holding the articulating film 14 if they extend in the longitudinal direction of the clamping surfaces 17.

What is claimed is:

1. A forceps comprising a pair of resilient parts (2, 3) having handle arms (5, 5) immovably fixedly secured to each other at a rear portion (4) thereof, said resilient parts (2, 3) being constructed and arranged to normally resiliently bias said handle arms (5, 5) away from each other, said handle arms (5, 5) merging in crossing relationship at medial portions (6, 7) with respective substantially parallel arms (8, 9), said parallel arms (8, 9) having respective substantially parallel clamping end portions (12, 12), said clamping end portion (12, 12) and said parallel arms (8, 9) defining therebetween an included angle α of at least 60°, and said handle arms (5, 5) being depressible against the resilient bias thereof to spread said clamping end portions (12, 12) into an open position and upon release of said handle arms (5, 5), the resilience thereof brings said clamping end portions (12, 12) into substantially parallel clamping relationship to an associated object therebetween.

2. The pair of forceps as defined in claim 1 wherein said included angle a is less than 90°.

3. The pair of forceps as defined in claim 1 wherein said parallel arms (8, 9) include adjacent parallel arm portions defining therebetween an excluded angle β of at least 150°.

4. The pair of forceps as defined in claim 1 wherein said clamping end portions (12, 12) include opposing gripping and clamping surfaces (17, 17).

5. The pair of forceps as defined in claim 1 wherein said clamping end portions (12, 12) include opposing gripping and clamping surfaces (17, 17) in the form of opposing substantially mirror images.

6. The pair of forceps as defined in claim 1 wherein said clamping end portions (12, 12) include opposing gripping and clamping surfaces (17, 17) in the form of opposing substantially mirror image concavo-convex surfaces.

7. The pair of forceps as defined in claim 1 wherein said clamping end portions (12, 12) include opposing gripping and clamping surfaces (17, 17) in the form of opposing substantially mirror image ribs and grooves.

8. The pair of forceps as defined in claim 1 wherein said parallel arms (8, 9) are each defined by parallel arms (8, 10 and 9, 11) respectively.

9. The pair of forceps as defined in claim 1 wherein said parallel arms (8, 9) are each defined by parallel arms (8, 10 and 9, 11) respectively, and said clamping end portions (12) are each defined by parallel end portions (12, 13).

10. The pair of forceps as defined in claim 9 wherein said included angle α is less than 90°.

11. The pair of forceps as defined in claim 9 wherein said parallel arms (8, 10; 9, 11) include adjacent parallel arm portions defining therebetween an excluded angle β of at least 150°.

12. The pair of forceps as defined in claim 9 wherein said clamping end portions (12, 12) include opposing gripping and clamping surfaces (17, 17).

13. The pair of forceps as defined in claim 9 wherein said clamping end portions (12, 12) include opposing gripping and clamping surfaces (17, 17) in the form of opposing substantially mirror images.

14. The pair of forceps as defined in claim 9 wherein said clamping end portions (12, 12) include opposing gripping and clamping surfaces (17, 17) in the form of opposing substantially mirror image concavo-convex surfaces.

15. The pair of forceps as defined in claim 9 wherein said clamping end portions (12, 12) include opposing gripping and clamping surfaces (17, 17) in the form of opposing substantially mirror image ribs and grooves.

16. A pair of forceps comprising a pair of resilient parts (2, 3) having arms (5, 5) immovably fixedly secured to each other at a rear portion (4) thereof, said handle arms (5, 5) being normally in substantially diverging relationship to each other in a direction away from said rear portion (4), said handle arms (5, 5) merging through crossing medial portions (6, 7) with respective pairs of substantially parallel arms (8, 10; 9, 11), said parallel arms (8, 10; 9, 11) having respective substantially parallel clamping end portions (12, 13) and said clamping end portions (12, 13), and said parallel arms (8, 10; 9, 11) defining therebetween an included angle of at least 60° but substantially less than 90°.

17. A pair of forceps comprising a pair of resilient parts (2, 3) having arms (5, 5) immovably fixedly secured to each other at a rear portion (4) thereof, said handle arms (5, 5) being normally in substantially diverging relationship to each other in a direction away from said rear portion (4), said handle arms (5, 5) merging through crossing medial portions (6, 7) with respective pairs of substantially parallel arms (8, 10; 9, 11), said parallel arms (8, 10; 9, 11) having respective substantially parallel clamping end portions (12, 13), said parallel arms (8, 10; 9, 11) adjacent said medial portions (6, 7) including parallel arm portions defining therebetween an excluded angle β of at least 150°; and said clamping end portions (12, 13) and said parallel arms (8, 10; 9, 11) defining therebetween an included angle of substantially 90°.

* * * * *